United States Patent
Fischer et al.

(10) Patent No.: US 10,081,584 B2
(45) Date of Patent: Sep. 25, 2018

(54) PROCESS FOR THE SEPARATION OF GLYCOLS

(71) Applicant: SHELL OIL COMPANY, Houston, TX (US)

(72) Inventors: Kai Jürgen Fischer, Amsterdam (NL); Waldo Eugene De Villiers, Katy, TX (US); Pieter Huizenga, Amsterdam (NL); Carmelo Perez Golf, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/536,270

(22) PCT Filed: Dec. 16, 2015

(86) PCT No.: PCT/EP2015/080107
§ 371 (c)(1),
(2) Date: Jun. 15, 2017

(87) PCT Pub. No.: WO2016/097064
PCT Pub. Date: Jun. 23, 2016

(65) Prior Publication Data
US 2017/0362150 A1    Dec. 21, 2017

Related U.S. Application Data

(60) Provisional application No. 62/093,780, filed on Dec. 18, 2014.

(51) Int. Cl.
*C07C 29/82* (2006.01)
*C07C 29/76* (2006.01)
*C07C 31/20* (2006.01)

(52) U.S. Cl.
CPC .............. *C07C 29/82* (2013.01); *C07C 29/76* (2013.01); *C07C 31/202* (2013.01); *C07C 31/205* (2013.01); *C07C 31/207* (2013.01)

(58) Field of Classification Search
CPC ...................................................... C07C 29/82
See application file for complete search history.

(56) References Cited

FOREIGN PATENT DOCUMENTS

| CN | 103772146 A | * | 5/2014 |
| CN | 103772148 A | * | 5/2014 |

OTHER PUBLICATIONS

Xiao, J. et al. Patent No. CN103772146A, May 2014, pp. 1-5; English translation (Year: 2014).*

(Continued)

*Primary Examiner* — Medhanit W Bahta

(57) ABSTRACT

The invention provides a process for the separation of MEG from a glycol stream comprising MEG and 1,2-BDO, said process comprising the steps of: (a) providing the glycol stream and an azeotrope-forming agent to a distillation column, (b) subjecting the glycol stream and the azeotrope-forming agent to distillation at a distillation temperature and a distillation pressure; (c) obtaining a first overhead stream comprising an azeotrope of MEG and the azeotrope-forming agent and a first bottoms stream comprising 1,2-BDO; and (d) subjecting the first overhead stream to phase separation in the presence of water to obtain an MEG-rich aqueous stream and an azeotrope-forming agent rich stream, wherein the azeotrope-forming agent is an organic solvent that forms a homogeneous azeotrope with MEG and does not form an azeotrope with 1,2-BDO at the distillation temperature and pressure.

8 Claims, 3 Drawing Sheets

(56) References Cited

OTHER PUBLICATIONS

Qi, w. et al. Patent No. CN103772148A, May 2014, pp. 1-3; English translation (Year: 2014).*

* cited by examiner

PROCESS FOR THE SEPARATION OF GLYCOLS

PRIORITY CLAIM

The present application is the National Stage (§ 371) of International Application No. PCT/EP2015/080107, filed Dec. 16, 2015, which claims priority from U.S. Patent Application No. 62/093,780, filed Dec. 18, 2014 incorporated herein by reference.

FIELD OF THE INVENTION

The present invention relates to a process for the selective separation of glycols.

BACKGROUND OF THE INVENTION

Ethylene glycol and propylene glycol are valuable materials with a multitude of commercial applications, e.g. as heat transfer media, antifreeze, and precursors to polymers, such as PET. Ethylene and propylene glycols are typically made on an industrial scale by hydrolysis of the corresponding alkylene oxides, which are the oxidation products of ethylene and propylene, produced from fossil fuels.

In recent years, increased efforts have focused on producing chemicals, including glycols, from renewable feedstocks, such as saccharide-containing feedstock.

The term saccharide-containing feedstock is used herein to mean any composition comprising mono-, di- and/or poly-saccharides derived from plant matter.

For example, US 2011/312050 describes a continuous process for the catalytic generation of polyols from cellulose, in which the cellulose is contacted with hydrogen, water and a catalyst to generate an effluent stream comprising at least one polyol.

CN 102643165 is directed to a catalytic process for reacting saccharides in an aqueous solution with hydrogen in the presence of a catalyst in order to generate polyols.

As with many chemical processes, the reaction product stream in these reactions comprises a number of desired materials as well as diluents, by-products and other undesirable materials. In order to provide a high value process, the desirable product or products must be obtainable from the reaction product stream in high purity with a high percentage recovery of each product and with as low as possible use of energy, chemical components and complex equipment.

In known processes to make glycols, the glycols are usually present at high dilution in a solvent, typically water. The water is usually removed from the glycols by distillation. Subsequent purification of the glycols is then carried out by fractional distillation.

When glycols are produced by hydrogenolysis of saccharide-containing feedstock, a mixture of glycols is produced. The main glycol constituents in the reaction product stream are monoethylene glycol (MEG), 1,2-monopropylene glycol (MPG) and 1,2-butanediol (1,2-BDO).

The separation of these glycols by fractional distillation is problematic due to the similarity in their boiling points, particularly between MEG and 1,2-BDO (197.3° C. and 195 to 196.9° C. respectively).

More particularly, the isolation of a pure MEG overhead stream by fractional distillation from a mixture comprising MEG and 1,2-BDO is made impossible by the formation of an azeotrope between MEG and 1,2-BDO at temperatures ranging from 20 to 250° C. and pressures ranging from 1 mbar to 3.5 bar.

A number of methods have been described in the art as suitable for separating MEG from a mixture of glycols.

US 2012/0184783 discloses several methods for the extraction of glycols from aqueous streams. In particular this document discloses methods for the selective extraction of individual glycols from concentrated mixtures thereof comprising less than 50 wt % water using a hydrophobic solvent mixture. Optionally, at least one of the hydrophobic solvents present in the mixture forms a heteroazeotropic mixture with MEG and, thus, allows further separation of the glycols.

U.S. Pat. No. 4,966,658 discloses azeotrope forming agents that enhance the relative volatility of ethylene glycol to enable its separation from aqueous mixtures of MEG and butanediols by subjecting such mixtures to hetroazeotropic distillation.

U.S. Pat. No. 5,423,955 discloses azeotrope forming agents that enhance the relative volatility of propylene glycol to enable its separation from 1,2-BDO by homoazeotropic distillation.

However, the molar ratio of the azeotrope forming agent to glycols used in the abovementioned cases is high for entrainers with a lower boiling point than the glycols, or the improvement of relative volatilities of MEG over 1,2-BDO is low for entrainers with a higher boiling point than the glycols, making the overall glycol production process expensive and more complicated to run.

Therefore, it would be advantageous to provide an improved method suitable for the recovery of MEG from mixtures comprising MEG and 1,2-BDO wherein the relative volatilities of MEG over 1,2-BDO is high enough and the amount of azeotrope forming agent used is low enough to make the overall glycol production process more economical than processes disclosed in the prior art.

SUMMARY OF THE INVENTION

Accordingly, the present invention provides a process for the separation of MEG from a glycol stream comprising MEG and 1,2-BDO, said process comprising the steps of: (a) providing the glycol stream and an azeotrope-forming agent to a distillation column, (b) subjecting the glycol stream and the azeotrope-forming agent to distillation at a distillation temperature and a distillation pressure; (c) obtaining a first overhead stream comprising an azeotrope of MEG and the azeotrope-forming agent and a first bottoms stream comprising 1,2-BDO; and (d) subjecting the first overhead stream to phase separation in the presence of water to obtain an MEG-rich aqueous stream and an azeotrope-forming agent rich stream, wherein the azeotrope-forming agent is an organic solvent that forms a homogeneous azeotrope with MEG and does not form an azeotrope with 1,2-BDO at the distillation temperature and pressure.

DETAILED DESCRIPTION OF THE INVENTION

Figure 1:
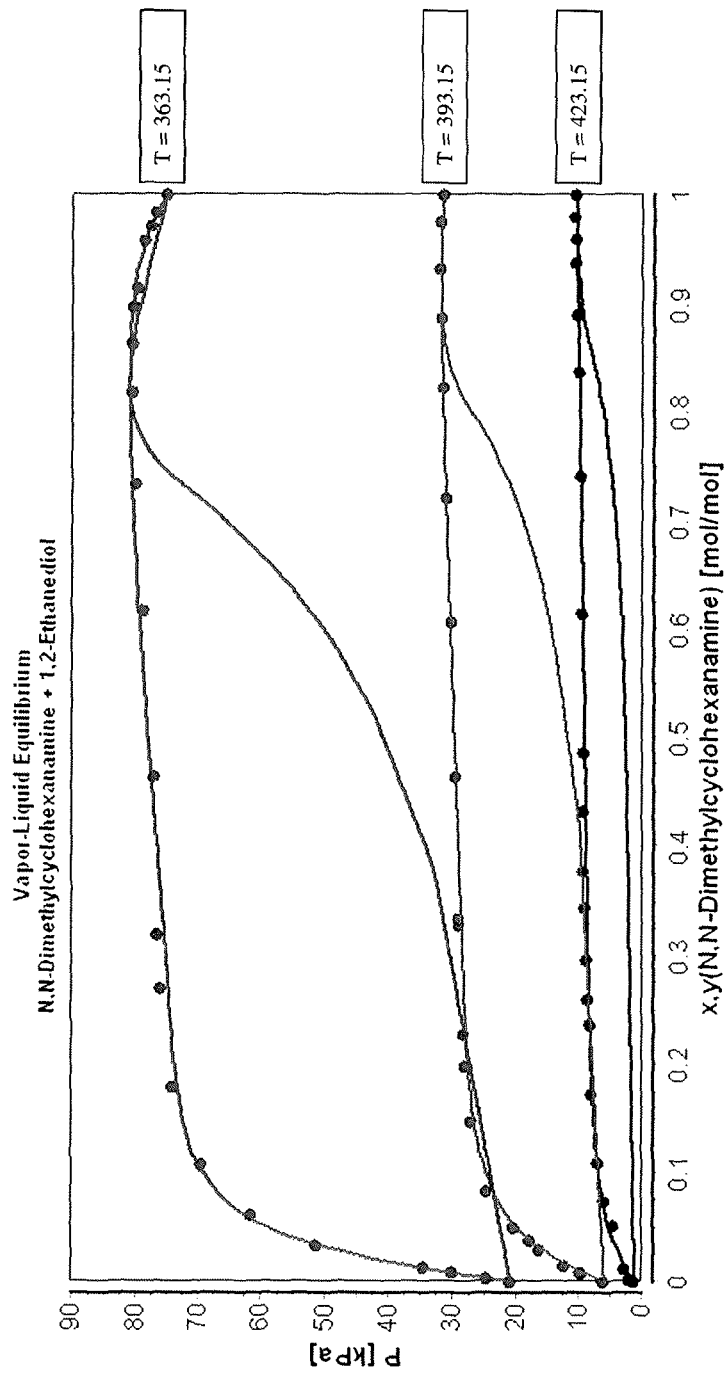
FIGS. 1 and 2 are graphs showing vapour-liquid equilibrium data for mixtures of MEG and 1,2-BDO with dimethyl cyclohexylamine (DMCA).

The present inventors have surprisingly found that MEG and 1,2-BDO present in a glycol stream may be selectively separated from each other, and from other components that may be present in the glycol, by distilling the mixture in the presence of an azeotrope-forming agent which forms an azeotrope of MEG and the azeotrope-forming agent with different volatility to 1,2-BDO. 1,2-BDO and the azeotrope of MEG and the azeotrope-forming agent may then be separated by fractional distillation. An overhead stream obtained from such distillation comprises the azeotrope of MEG and the azeotrope-forming agent, which is then subjected to phase separation in the presence of water to provide an MEG-rich aqueous stream that can be separated from a stream rich in the azeotrope-forming agent.

The term glycol is herein given its usual meaning, i.e. a diol in which the two hydroxyl groups are present on vicinal carbon atoms.

Optionally, the glycol stream also may contain monopropylene glycol (MPG). Also optionally, the glycol stream may contain an aqueous or organic solvent, preferably water.

Preferably, the glycol stream is a reaction product stream from a process for the production of glycols, or is derived from such a reaction product stream. In a particularly preferred embodiment of the invention, the glycol stream comprising MEG and 1,2-BDO is the reaction product stream from a process for the hydrogenolysis of a saccharide-containing feedstock, or is derived therefrom.

In the embodiment of the invention wherein the glycol stream is the reaction product stream from a process for the hydrogenolysis of a saccharide-containing feedstock, or is derived therefrom, the glycol stream may also comprise hydrogenolysis reaction by-products, amounts of the reaction catalyst and its degradation products, as well as other undesirable materials.

Typically, the reaction product stream from a process for the hydrogenolysis of a saccharide-containing feedstock comprises, as glycols, at least MEG, MPG and 1,2-BDO. These glycols are typically present at a concentration in the range of from 0.1 to 30 wt % of the overall stream.

In such a reaction stream, MEG is suitably present as at least 10 wt %, preferably as at least 30 wt % of the non-aqueous fraction of the stream. MEG is suitably present as at most 90 wt %, preferably as at most 80 wt % of the non-aqueous fraction of the stream.

In such a reaction stream, MPG is suitably present as at least 8 wt %, preferably as at least 10 wt % of the non-aqueous fraction of the stream. MPG is suitably present as at most 45 wt %, preferably as at most 20 wt % of the non-aqueous fraction of the stream.

In such a reaction stream, 1,2-BDO is suitably present as at least 2 wt %, preferably as at least 6 wt % of the non-aqueous fraction of the stream. 1,2-BDO is suitably present as at most 20 wt %, preferably as at most 8 wt % of the non-aqueous fraction of the stream.

As well as the glycols, the reaction product streams from hydrogenolysis reactions of saccharides may comprise water, oxygenates, hydrocarbons, catalyst, degradation products, and gases in any composition. The variety of compounds and their concentration depend on the saccharide-containing feedstock and the various hydrogenation and hydrogenolysis conversion conditions, including catalysts, reaction conditions such as temperature, pressure and saccharide concentration. However, suitably the hydrogenolysis reactions have gone to completion and the aqueous stream contains less than 5 wt %, preferably less than 2 wt %, more preferably less than 1 wt %, even more preferably less than 0.5 wt %, most preferably substantially no saccharides when considered as a weight percentage of the overall stream. Typically, the aqueous stream also contains less than 5 wt %, preferably less than 2 wt %, more preferably less than 1 wt %, even more preferably less than 0.5 wt %, most preferably substantially no glycerol, when considered as a weight percentage of the overall stream.

If the first mixture comprising MEG and 1,2-BDO is derived from such a reaction product stream, one or more treatment, separation and/or purification steps may be applied to the reaction product stream before the process of the present invention. Such steps may include one or more of: removal of at least a portion of the solvent present, for example by distillation; removal of light ends; fractional distillation to produce a glycols stream and removal of heavy organics and any inorganics present, such as catalyst material; and initial separation steps to achieve preliminary separation of glycols, e.g. separation of MPG by fractional distillation or other distillation process that results in a stream in which essentially all of the glycols remaining are MEG and 1,2-BDO, with trace amounts of higher glycols, such as 2,3-butanediol, 1,2-pentanediol and 1,2-hexanediol.

The glycol stream comprising MEG and 1,2-BDO preferably has a weight ratio of MEG:1,2-BDO of at least 5:1. More preferably the weight ratio of MEG:1,2-BDO is at least 25:1. Optionally, MPG is also present in the mixture comprising MEG and 1,2-BDO, In this embodiment of the invention, MPG typically comprises in the range of from 2 to 45 wt % of the mixture comprising MEG and 1,2-BDO.

The azeotrope-forming agent comprises an organic solvent that forms a homogeneous azeotrope with MEG and does not form an azeotrope with 1,2-BDO at the distillation temperature and pressure. Preferably, the azeotrope-forming agent is an organic solvent containing an aliphatic cyclic element and one or two heteroatoms, selected from oxygen and nitrogen. Further, the azeotrope-forming agent preferably has a boiling point in the range of from 140° C. to 180° C. One example of such an azeotrope-forming agent is dimethylcyclohexylamine (DMCA).

The amount of azeotrope-forming agent suitably provided to the distillation column with the glycol stream will depend on the distillation temperature and pressure and will be readily determined by the skilled person. Preferably, the amount of azeotrope-forming agent suitably provided to the distillation column is such that the molar ratio of DMCA:MEG is at most 10:1. Preferably, the amount of azeotrope-forming agent provided to the distillation column with the glycol stream is such that the molar ratio of DMCA:MEG is at least 1:1.

The azeotrope-forming agent is preferably provided to the distillation column via a feed tray in the lower part of said column.

The glycol stream and the azeotrope-forming agent are subjected to distillation at a distillation temperature and pressure. Preferably, the distillation pressure is in the range of from 0.1 kPa to 350 kPa, more preferably in the range of from 50 to 150 kPa. Preferably, the distillation temperature is in the range of from 20 to 250° C., more preferably in the range of from 160 to 230° C.

A first overhead stream comprising an azeotrope of MEG and the azeotrope-forming agent is obtained from the top of the distillation column. Preferably at least 70 wt %, more preferably at least 80 wt %, even more preferably at least 90 wt %, most preferably at least 95 wt % of the MEG present in the glycol stream is present in said overhead stream.

The first overhead stream is subjected to phase separation in the presence of water to obtain an MEG-rich aqueous stream and an azeotrope-forming agent rich stream.

In an embodiment of the invention, at least a portion of said water is provided to the overheads stream after distillation, for example by injecting water into the distillate condensate.

In an embodiment of the invention at least a portion of said water is present in the glycols stream and is obtained as part of the overheads stream.

Preferably, the water is present in an amount such that the molar ratio of water:azeotrope-forming agent is in the range of from 1:50 to 1:1.

Phase separation may be carried out by allowing the two phases to settle by gravity and then separating them by standard methods. Optionally, this may be carried out with the application of heat, preferably such that the phases are at a temperature of at least 60° C.

The MEG rich aqueous stream may be further purified by using methods such as fractional distillation to remove water and minor impurities that may have carried over with the MEG.

The azeotrope-forming agent rich stream may be recycled to the distillation column.

The bottoms stream comprises 1,2-BDO. This may be subjected to further purification, e.g. distillation, steps in order to provide product grade 1,2-BDO.

In embodiments of the invention wherein MPG is present in the glycol stream, the first bottoms stream recovered from the fractional distillation may also comprise MPG. The MPG and 1,2-BDO may then be separated from each other by a separate fractional distillation step. These embodiments are likely to occur wherein the distillation is carried out at lower distillation temperatures and pressures.

Alternatively, in embodiments of the invention wherein MPG is present in the glycol stream, MPG may be present in the first overhead stream. The MPG and MEG will then both be present in the MEG-rich aqueous stream and may then be separated from each other by a separate fractional distillation step. These embodiments are likely to occur wherein the distillation is carried out at higher distillation temperatures and pressures.

Also alternatively, in embodiments of the invention wherein MPG is present in the glycol stream, MPG may be present in both the bottoms stream and the overhead stream.

DETAILED DESCRIPTION OF THE INVENTION

Figure 2:
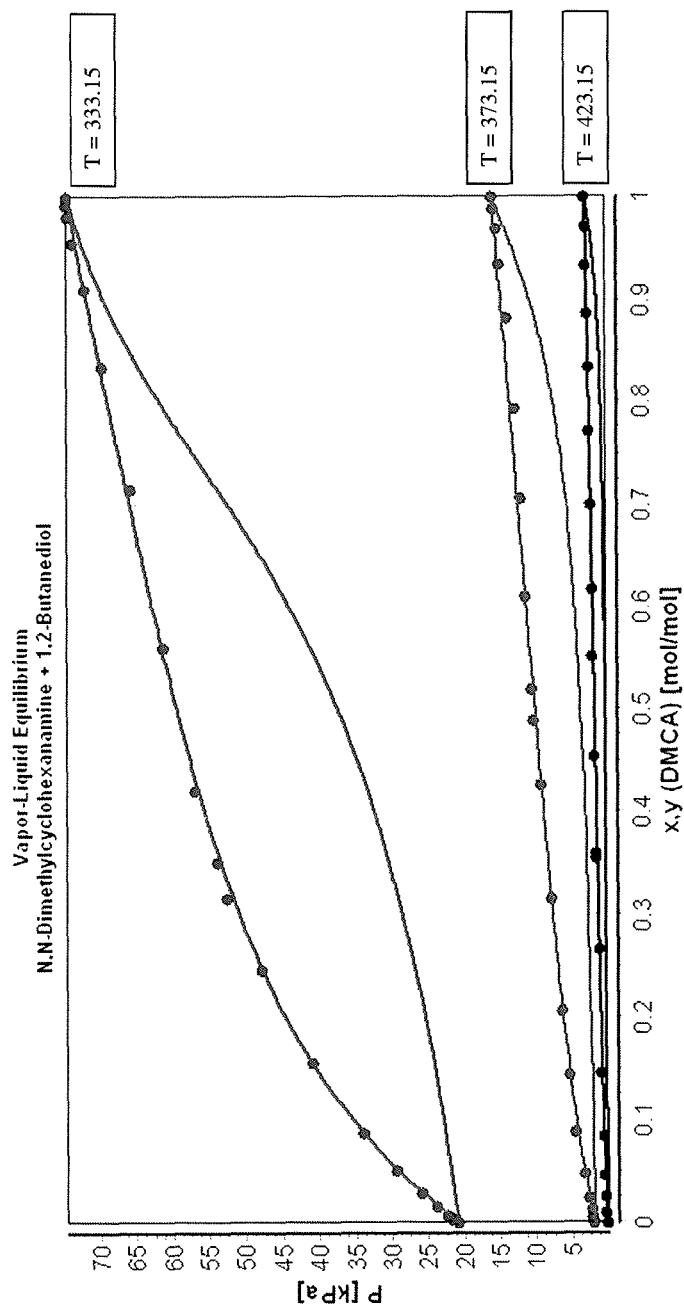

FIGS. 1 and 2 are graphs showing vapour-liquid equilibrium data for mixtures of MEG and 1,2-BDO with dimethyl cyclohexylamine (DMCA). Mixtures of the glycols and DMCA were prepared with varying ratio of glycol:DMCA. The resulting boiling point (bubble point) pressures were measured at each temperature. The corresponding dew point data points are shown in the smooth lines.

Figure 3:
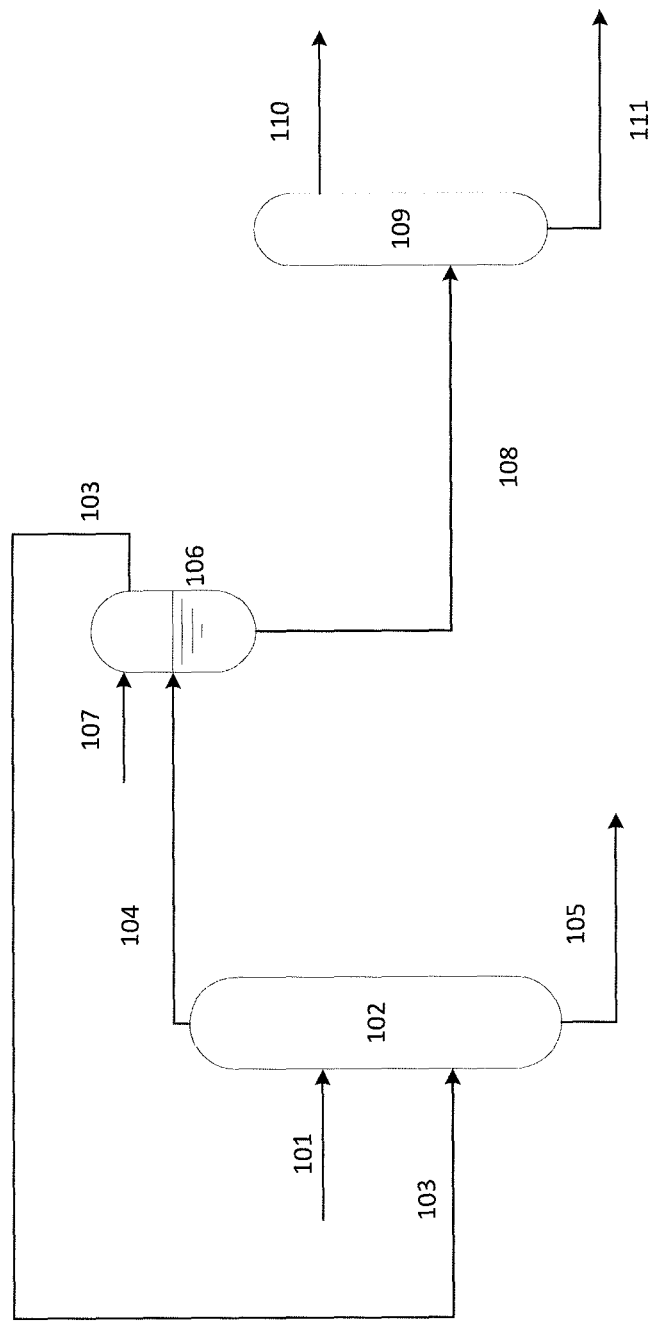
FIG. 3 show a non-limiting embodiment of the process of the present invention.

FIG. 3 shows an exemplary, but non-limiting, embodiment of the present invention. A glycol feed 101 comprising MEG and 1,2-BDO is provided to a distillation column 102. Also provided to the distillation column is an azeotrope-forming agent feed 103. The feeds are subjected to distillation resulting in an overhead stream 104 comprising an azeotrope of MEG and the azeotrope-forming agent. A bottoms stream 105, comprising 1,2-BDO is also obtained from the distillation column 102. The overhead stream 104 comprising an azeotrope of MEG and the azeotrope-forming agent is provided to phase separator 106 and a water feed 107 is added, if necessary. Phase separation is carried out to provide an azeotrope-forming agent rich stream 103, which is recycled to the distillation column 102 as feed 103, and a MEG-rich aqueous stream 108 which is subjected to distillation 109 to remove a water stream 110 and provide an MEG stream 111.

That which is claimed is:

1. A process for the separation of MEG from a glycol stream comprising MEG and 1,2-BDO, said process comprising the steps of: (a) providing the glycol stream and an azeotrope-forming agent to a distillation column, (b) subjecting the glycol stream and the azeotrope-forming agent to distillation at a distillation temperature and a distillation pressure; (c) obtaining a first overhead stream comprising an azeotrope of MEG and the azeotrope-forming agent and a first bottoms stream comprising 1,2-BDO; and (d) subjecting the first overhead stream to phase separation in the presence of water to obtain an MEG-rich aqueous stream and an azeotrope-forming agent rich stream, wherein the azeotrope-forming agent is an N,N-dimethylcyclohexylamine that forms a homogeneous azeotrope with MEG and does not form an azeotrope with 1,2-BDO at the distillation temperature and pressure.

2. A process according to claim 1, wherein the glycol stream also comprises MPG.

3. A process according to claim 1, wherein the glycol stream is the reaction product stream from a process for the hydrogenolysis of a saccharide-containing feedstock or is derived therefrom.

4. A process according to claim 1, wherein the amount of azeotrope-forming agent provided to the distillation column is such that the molar ratio of azeotrope-forming agent to MEG is at most 10:1 and at least 1:1.

5. A process according to claim 1, wherein the distillation temperature is in the range of from 20 to 250° C.

6. A process according to claim 1, wherein the distillation pressure is in the range of from 0.1 to 350 kPa.

7. A process according to claim 1, wherein the phase separation of the first overheads stream is carried out at a water to azeotrope-forming agent molar ratio in the range of from 1:50 to 1:1.

8. A process according to claim 1, wherein the phase separation is carried out a temperature of at least 60° C.

* * * * *